US008086407B2

(12) United States Patent
Chan et al.

(10) Patent No.: US 8,086,407 B2
(45) Date of Patent: Dec. 27, 2011

(54) METHOD AND DEVICE FOR ENVIRONMENTAL MONITORING

(75) Inventors: Yiu Wai Chan, Hong Kong (HK); Sui Chun Law, Hong Kong (HK)

(73) Assignee: AKOS Advanced Technology Ltd, Shatin N.T. (HK)

( * ) Notice: Subject to any disclaimer, the term of this patent is extended or adjusted under 35 U.S.C. 154(b) by 344 days.

(21) Appl. No.: 12/281,824

(22) PCT Filed: Mar. 7, 2007

(86) PCT No.: PCT/CN2007/000736
§ 371 (c)(1),
(2), (4) Date: Sep. 5, 2008

(87) PCT Pub. No.: WO2007/104240
PCT Pub. Date: Sep. 20, 2007

(65) Prior Publication Data
US 2009/0048781 A1   Feb. 19, 2009

(51) Int. Cl.
*G01V 3/00* (2006.01)
*F24F 3/14* (2006.01)
(52) U.S. Cl. ......................................... 702/2; 236/44 C
(58) Field of Classification Search ................... 702/1–2, 702/22–24, 26–27, 30, 33, 57, 65, 81, 84, 702/99, 127–128, 130–131, 136, 182–183, 702/189; 236/44 A, 44 C, 44 R, 49.1–49.3; 165/58, 201, 211, 222–223, 248, 253, 257; 454/229, 256–258; 340/573, 628, 632–634
See application file for complete search history.

(56) References Cited

U.S. PATENT DOCUMENTS
5,261,596 A * 11/1993 Tachibana et al. ........... 236/49.3

FOREIGN PATENT DOCUMENTS
| JP | 2-254396 | 10/1990 |
| JP | 05-142173 | 6/1993 |
| JP | 05142173 A * | 6/1993 |
| JP | 2003-106904 | 4/2003 |

OTHER PUBLICATIONS

Daikin Ind Ltd, JP 05142173 A, Jun. 8, 1993, English version.*
Japanese Patent Application Examination Report for Application No. P2008-558619, dated Aug. 9, 2011, 5 pgs.

* cited by examiner

*Primary Examiner* — Michael Nghiem
*Assistant Examiner* — Toan M Le
(74) *Attorney, Agent, or Firm* — Kauth, Pomeroy, Peck & Bailey LLP

(57) ABSTRACT

The present invention is related to an environmental monitoring and analyzing device. The device contains a plurality of sensors, a control unit and a display unit. The different types of sensors obtain values of different environmental parameters. The control unit receives the obtained values of the environmental parameters and compares the obtained values against predetermined standards and criteria which define parameter ranges of the different environmental parameters. A display unit displays a real-time air quality report including a user-friendly interpretation of the obtained values and recommendations in response to the obtained values. By implementing this invention into an embodiment, the environmental monitoring analyzing is carried out instantly by considering the interrelationship of the obtained values of the different environmental parameters. A real-time comprehensive and easily understood by non-technical user air quality report is provided.

11 Claims, 9 Drawing Sheets

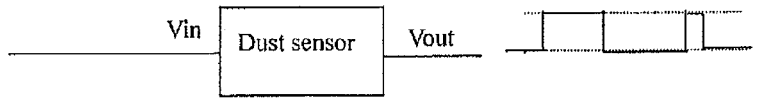

Figure 8

| Measured Parameter | Parameter Ranges | Message of the First Recommendation |
|---|---|---|
| Concentration of Carbon Dioxide (ppm) | 1,000 to <5,000 | Turn on air exhausting system |
| | 5,000 or above | Turn on air exhausting system<br>Decrease the number of occupants<br>Open the windows |
| Concentration of Carbon Monoxide ($\mu g/m^3$) | 10,000 to <29,000 | Turn on air exhausting system<br>Open the windows<br>Do no smoke<br>Turn off the combustion oven or device<br>Leave this place immediately |
| | 29,000 or above | Turn on air exhausting system<br>Open the windows<br>Do no smoke<br>Turn off the combustion oven or device<br>Leave this place immediately |
| Level of Respirable Suspended Particulates ($\mu g/m^3$) | 180 or above | Turn on air filtration device |
| Concentration of Total Volatile Organic Compounds ($\mu g/m^3$) | 600 or above | Turn on air filtration device |
| Temperature (°C) | >25.5 | Turn on air cooling device |
| | <20°C | Turn off air cooling device |
| | <10°C | Turn on air warming device |
| Relative Humidity (%) | <40% | Turn on humidifier |
| | >70% | Turn on dehumidifier |

Figure 9

| Message of the potential problem | First conditional array | Second conditional array | Third conditional array | Forth Conditional array |
|---|---|---|---|---|
| Pay attention to concentration of formaldehyde | i.) Temperature: 25.5 to <35°C and<br>ii.) Level of total volatile organic compound: 600 μg/m³ above | i.) Temperature: 25.5 to <35°C and<br>ii.) Level of total volatile organic compound: 3000μg/m³ above | I.) Level of total volatile organic compound: 600 to <3000μg/m³ | i.) Level of total volatile organic compound: 3000 to <25000 μg/m³ above |
| Pay attention to poor air exhausting conditions | i.) Concentration of carbon dioxide: 1,000 to <5,000ppm | i.) Concentration of carbon dioxide: 5,000ppm above | -- | -- |
| Pay attention to sources which irritate the eyes and the respiration system | i.) Temperature: 25.5 to <35°C and<br>ii.) Relative humidity: 70 to 100% and<br>iii.) Level of total volatile organic compound: 600 μg/m³ above | i.) Temperature: 25.5 to <35°C and<br>ii.) Relative humidity : 70 to 100% and<br>iii.) Level of total volatile organic compound: 3000μg/m³ or above | -- | -- |
| Pay attention to the operation condition of air filtration device | i.) Relative humidity : <40% and<br>ii.) Level of respirable suspended particulates 180 to 20,000 μg/m³ | i.) Relative humidity :<40% and<br>ii.) Level of respirable suspended particulates 20,000 μg/m³ or above | I.) Level of respirable suspended particulates 180 to 20,000 μg/m³ | i.) Level of respirable suspended particulates 20,000 μg/m³ or above |
| Pay attention to the radon level in air | i.) Concentration of carbon dioxide: 1,000 to <5,000ppm | i.) Concentration of carbon dioxide: 5,000ppm or above | -- | -- |
| Pay attention to the airborne bacteria level | i.) Concentration of carbon dioxide: 1,000 to 5,000ppm and<br>ii.) Temperature 22 to <35°C and<br>iii.) Relative humidity : 50 to 100% and<br>iv.) Level of respirable suspended particulates 20 to 80 μg/m³ | i.) Concentration of carbon dioxide: 5,000ppm above and<br>ii.) Temperature 22 to < 35°C and<br>iii.) Relative humidity : 50 to 100% and<br>iv.) Level of respirable suspended particulates 180 to 20,000 μg/m³ or above | i.) Concentration of carbon dioxide: 5,000ppm above and<br>ii.) Temperature 22 to <35°C and<br>iii.) Relative humidity : 50 to 100% and<br>iv.) Level of respirable suspended particulates 20,000 μg/m³ or above | -- |
| Pay attention to the number of indoor occupant | i.) Concentration of carbon dioxide: 1,000 to <5,000ppm | i.) Concentration of carbon dioxide : 5,000ppm above and<br>ii.) Level of total volatile organic compound: 600 to 3000μg/m³ | i.) Concentration of carbon dioxide : 1,000 to <5,000ppm above and<br>ii.) Level of total volatile organic compound: 3000μg/m³ above | -- |
| Pay attention to level of nitrogen monoxide | i.) Concentration of carbon monoxide: 10,000 to<29,000μg/m³ | i.) Concentration of carbon monoxide: 29,000μg/m³ or above | -- | -- |

Figure 10

| Message of the potential problems | Recommendation to address the potential problems |
|---|---|
| Pay attention to concentration of formaldehyde | Open the windows<br>Turn on air filtration device<br>Turn on air exhausting system<br>Do not smoke |
| Pay attention to poor air exhausting conditions | Open the windows<br>Turn on air filtration device<br>Decrease the number of indoor occupant |
| Pay attention to sources which irritate the eyes and the respiration system | Open the windows<br>Turn on air filtration device<br>Turn on air exhausting system<br>Decrease the number of indoor occupant<br>Turn on ventilation fan<br>Turn on dehumidifier |
| Pay attention to the operation condition of air filtration device | Turn on air filtration device<br>Turn on humidifier<br>Wear the mask |
| Pay attention to the radon level in air | Open the windows<br>Turn on air exhausting system |
| Pay attention to the airborne bacteria level | Turn on air filtration device<br>Turn on air exhausting system<br>Carry out disinfection and cleaning works<br>Wear the mask<br>Remove dust by vacuum cleaner<br>Decrease the number of indoor occupant |
| Pay attention to the number of indoor occupant | Open the windows<br>Turn on air filtration device<br>Decrease the number of indoor occupant<br>Turn on air exhausting system<br>Turn on ventilation fan |
| Pay attention to level of nitrogen monoxide | Open the windows<br>Do not smoke<br>Check the combustion oven and device<br>Leave this place immediately |

Figure 11

| Measured Parameter | Low level | Middle Low Level | Middle high Level | High Level |
|---|---|---|---|---|
| Concentration of Carbon Dioxide (ppm) | <800 (A) | 800 to <1,000 (B) | 1,000 to <5,000 (C) | 5,000 or above (D) |
| Concentration of Carbon Monoxide ($\mu g/m^3$) | <2,000 (A) | 2,000 to <10,000 (B) | 10,000 to <29,000 (C) | 29,000 or above (D) |
| Level of Respriable Suspended Particulates ($\mu g/m^3$) | <20 (A) | 20 to <180 (B) | 180 to <20,000 (C) | 20,000 or above (D) |
| Concentration of Total Volatile Organic Compounds ($\mu g/m^3$) | <200 (A) | 200 to <600 (B) | 600 to <3,000 (C) | 3,000 or above (D) |
| Temperature (°C) | <20 (B) | 20 to <25.5 (A) | 25.5 to <30 (C) | 30 to <35 (D) |
| Relative Humidity (%) | <40 (B) | 40 to <70 (A) | 70 to <85 (C) | 85 to <100 (D) |

Figure 12

| Base on four different levels or measured parameters | Air Quality Message |
|---|---|
| Six A grades | Excellence |
| Only A grades and B grades | Good |
| Six B grades | Good |
| Only A grades, B grades, and C grades, but no D grade | Fair |
| Six C grades | Fair |
| A grades, B grades, C grades and D grades present at the same time | Poor |
| Six D grades | Poor |

Figure 13

METHOD AND DEVICE FOR ENVIRONMENTAL MONITORING

TECHNICAL FIELD

The present invention is related to the technology of environmental monitoring. More specifically, it is related to a device and a method for environmental monitoring and analyzing.

BACKGROUND

As the problems of indoor air pollution are getting severe, the public concerns on the conditions of their living and working environment as well as the health effects by the indoor air quality are increasing. At the same time, the guidelines and the rules to control and regulate the indoor air quality have been established in different countries. Hence, the demand for instruments and equipment on monitoring the air quality is increasing.

Conventionally, there are two major types of instruments for monitoring the indoor air quality. The first type of environmental monitoring instruments is employed mainly in the research laboratories. They are of considerably large scale. The second type belongs to the portable survey type instruments and they are much more compact in size.

The results obtained by the first type of environmental monitoring instrument are highly precise and accurate. Nevertheless, the prices of this type of instruments are significantly high. The operations of these instruments are complicated and only manageable by well trained and skillful technicians.

Generally speaking, each second type environmental monitoring instrument is equipped with a sensor for measuring a particular environmental parameter. The size of this type of instrument is therefore comparatively compact. Nevertheless, as different environmental parameters are inter-correlated, the level of a single parameter is usually affected by the levels of the other parameters. To obtain the level of a particular environmental parameter with a single sensor is usually not an all-round method. The precision obtained would be low. For examples, to measure the concentration of the volatile organic compounds solely by the photo-ionization detection method may give an inaccurate result as the detection method is easily affected by the temperature and relative humidity of the environment. In addition, different types of sensors with different working principles give different outcomes when they are employed for monitoring the same environmental parameter. For these reasons, there are usually difficulties to standardize the detection methods for the environmental parameters. In order to ensure an adequate and a moderately accurate result can be obtained for a single parameter, several instruments are usually brought to site during measurement. The results obtained are then evaluated together during analysis. The measurement processes by multiple instruments are rather inconvenience.

Nevertheless, for both types of environmental monitoring instruments being mentioned, only the raw data would be simply displayed and output. None of them would provide systematically analyzed information as described in the present invention.

SUMMARY OF THE INVENTION

At least one advantage of the present invention is to address the deficiencies of current environmental monitoring devices and methods, It has the further advantage to provide a device and a method for environmental monitoring and analyzing. Different levels of the environmental parameters are detected and measured at the same time. They are then judged and analyzed systematically. A real time and comprehensive air quality report is generated. The construction of the device is simple. It is easy to be operated even by the non-technical users. The environmental parameters evaluated are highly accurate and precise.

The present invention provides a device to monitor the environment, and to solve the problems by the conventional environmental monitoring instruments. The environmental monitoring device, comprising:
   a plurality of sensors being of different types, the different types of sensor obtaining values of different environmental parameters;
   a control unit to receive the obtained values of the environmental parameters and to compare the obtained values against predetermined standards and criteria which define parameter ranges of the different environmental parameters; and
   a display unit to display a real-time air quality report comprising a user-friendly interpretation of the obtained values based on the parameter ranges and recommendations in response to the obtained values based on the parameter ranges that is easily understood by a non-technical user;
wherein real-time analysis of the obtained values of the different environmental parameters is performed by considering the interrelationship of the obtained values of the different environmental parameters in order to interpret the obtained values and make recommendations based on the obtained values.

The predetermined standards and criteria includes a first judgment principle, the first judgment principle defining at least two parameter ranges for each environmental parameter, and corresponding recommendations for each parameter range.

The predetermined standards and criteria includes a second judgment principle, the second judgment principle defining at least one conditional array, the at least two parameter ranges defined by the first judgment principle for use as the parameter ranges for defining each conditional array, and a message corresponding to potential problems for each conditional array is provided.

Besides, the device further comprising recommendations to address the potential problems.

The predetermined standards and criteria includes a third judgment principle, the third judgment principle defining at least two categories for each environmental parameter, and air-quality-level judgment standards for air quality levels are defined based on the combination of different categories of the measured environmental parameters, and a message corresponding to air quality level by the air-quality-level judgment standards is provided.

The environmental parameter is any one from the group consisting of: temperature, relative humidity, volatile organic compounds, carbon monoxide, carbon dioxide, dust, ozone, carbon dioxide, air flow rate, radon, and formaldehyde.

The control unit of the device comprises:
   a power supply;
   control circuit;
   input circuits;
   output circuit;
   a central processing unit; and
   a memory to store the predetermined standards and criteria for judging the environmental parameters, messages corresponding to interpretations, recommendations and potential problems of the parameter ranges;

the power supply and control circuit connecting an external power supply to the device;

the input circuit collecting the obtained values from the sensors and outputting them to the central processing unit;

the central processing unit analyzing the obtained values based on the predetermined standards and criteria and defining the parameter ranges of each environmental parameter, and to output the interpretation and recommendations of each parameter range for display by the display unit.

The input circuit includes an analog to digital converter and a low pulse timer.

The present invention also offers a method to monitor and analyze the environment, comprising:

obtaining values of environmental parameters;

comparing the obtained values of the environmental parameters against predetermined standards and criteria which define parameter ranges of the different environmental parameters; and displaying a real-time air quality report comprising a user-friendly interpretation of the obtained values based on the parameter ranges and recommendations in response to the obtained values based on the parameter ranges that is easily understood by a non-technical user;

wherein real-time analysis of the obtained values of the different environmental parameters is performed by considering the interrelationship of the obtained values of the different environmental parameters in order to interpret the obtained values and make recommendations based on the obtained values.

The predetermined standards and criteria of the mentioned method includes a first, second and third judgment principle, the first judgment principle defining parameter ranges for the environmental parameters, corresponding recommendations for each parameter range are provided;

the second judgment principle defining conditional arrays, and at least two parameter ranges defined by the first judgment principle for use as parameter ranges for defining each conditional array, a message corresponding to potential problems and recommendations to address the potential problems for each conditional array are provided;

the third judgment principle defining at least two categories for each environmental parameter, and air-quality-level judgment standards for air quality levels are defined based on the combination of different categories of the obtained values, and a message corresponding to air quality level by the air-quality-level judgment standards is provided.

The environmental parameter is any one from the group consisting of: temperature, relative humidity, volatile organic compounds, carbon monoxide, carbon dioxide, dust, ozone, carbon dioxide, air flow rate, radon, and formaldehyde.

In the present invention, the values of different environmental parameters are obtained by different sensors, Real-time analysis of the obtained values of the different environmental parameters is performed by considering the interrelationship of the obtained values of the different environmental parameters.

A real-time air quality report is provided. The real-time air quality report comprising a user-friendly interpretation of the obtained values and recommendations in response to the obtained values that is easily understood by a non-technical user. (In other words, the report includes the message corresponding to the potential problems based on the parameter ranges, the recommendations to address the potential problems and the message corresponding to the air quality level.)

For certain environmental parameters, such as airborne bacteria and fungi, which need longer testing time by conventional methods They need hours for incubations by the conventional methods, the present invention would be able to provide an instant level assessment by means of forecasting, based on the (interrelationship/correlation) between different measured environmental parameters. For instance, in a warm and humid environment where the dust level has reached a certain high level (in an environment where the level of respirable suspended particulates is high), the prerequisite conditions for growing and incubating the airborne bacteria are actually created. Based on the values of the temperature, relative humidity and level of respirable suspended particulates, the level of airborne bacteria can then be forecasted simultaneously. On another example, in an environment where the concentration of the carbon dioxide is sustained at high level, poor ventilation or too many occupants are implied. With the present invention, a user-friendly interpretation of the obtained value of the environment would be generated. The user-friendly interpretation could be the messages of recommendations such as "turn on the air exhausting system", "decrease the number of occupants", "open the windows" etc. The device by the present invention is structurally simple and low cost. The device can be handled by non-technical users easily.

The following figures and description reveal the further details of the present invention.

BRIEF DESCRIPTION OF THE DRAWINGS

FIG. 8 depicts a circuit diagram for dust sensor in the environmental device of the present invention;

FIGS. 9 to 13 depict examples of the parameter judgment standards and criteria, as well as the resulted implications.

DETAILED DESCRIPTION OF THE DRAWINGS

Figure 1:
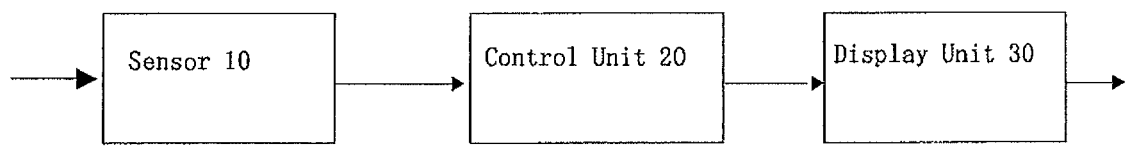
FIG. 1 illustrates circuit modules of the environmental device of the present invention.
Figure 2:
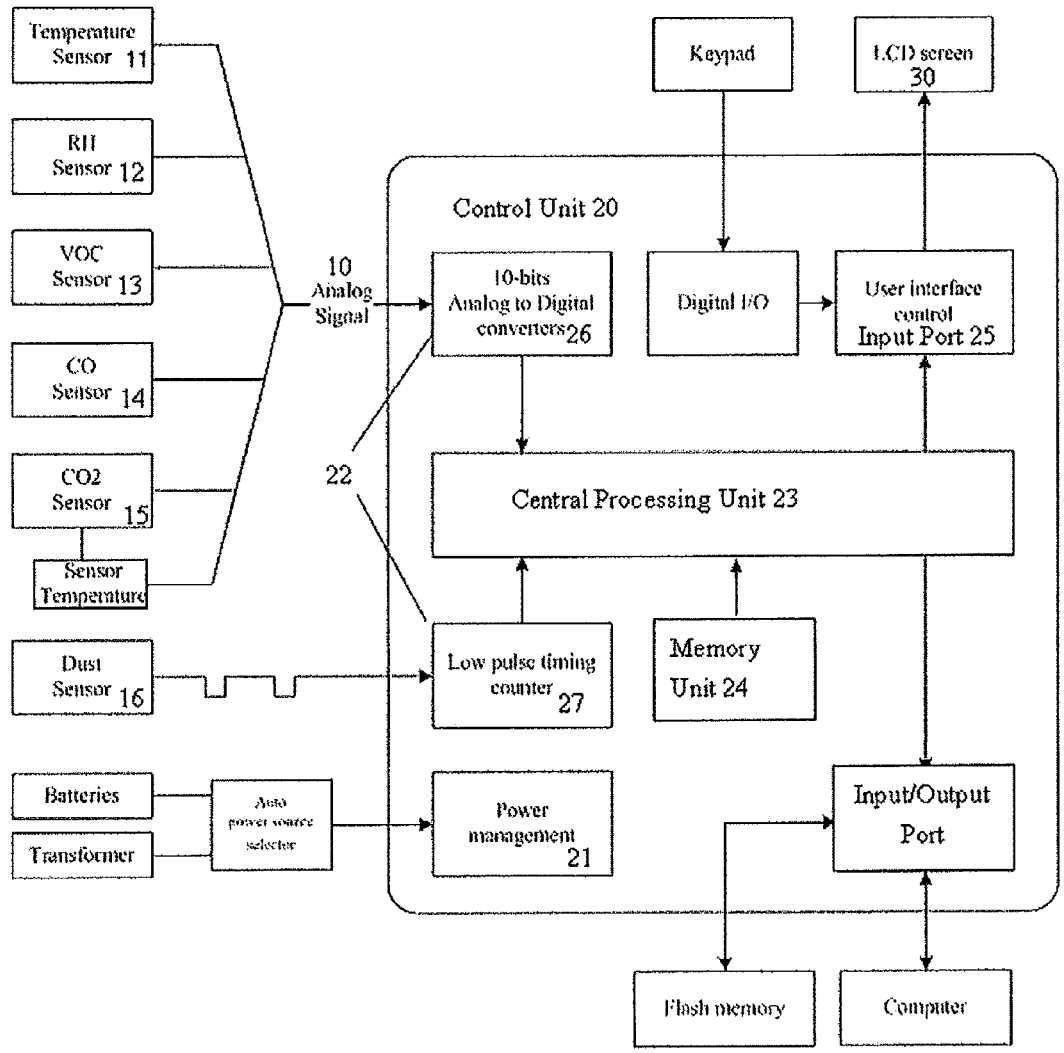
FIG. 2 depicts a block circuit diagram of the environmental device of the present invention.

Referring to FIGS. 1 and 2, the device of the present invention contains the sensors 10, the control unit 20 and the display unit 30.

The sensors 10 obtain the values of different environmental parameters. The control unit 20 collects the obtained values. In the present embodiment, the sensors 10 are a temperature sensor, a relative humidity sensor 12, a volatile organic compounds sensor 13, a carbon monoxide sensor 14, a carbon dioxide sensor 15, and a respirable suspended particulates sensor 16. Other environmental sensors such as the ozone sensor, the nitrogen dioxide sensor, the air flow rate sensor, the radon level sensor and the formaldehyde sensor can be applied for the same purpose.

Figure 3:
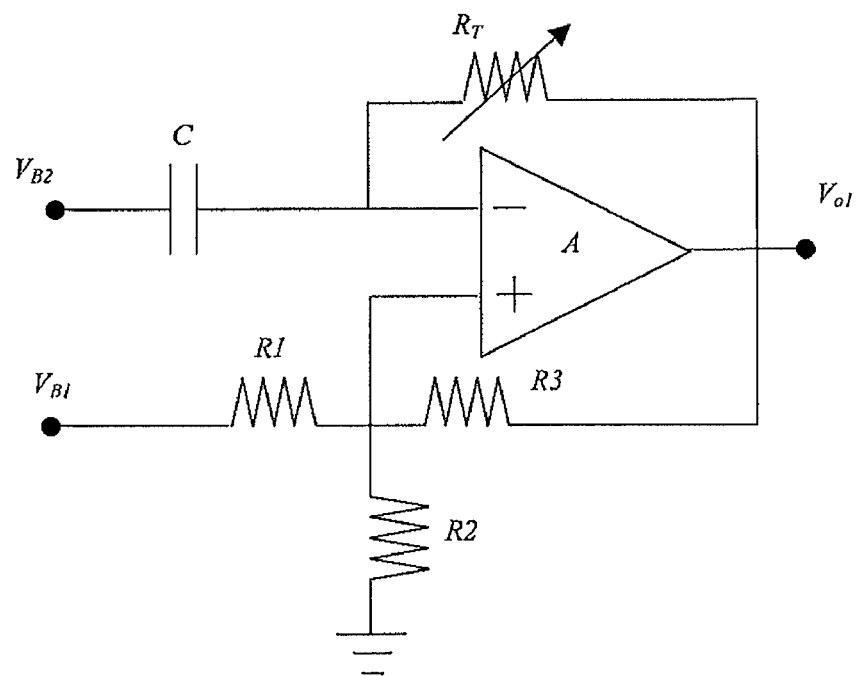
FIG. 3 depicts a circuit diagram for temperature sensor in the environmental device of the present invention.

FIGS. 3-8 indicate the circuit diagrams for the sensors in the embodiment of the present invention. The circuit for the temperature sensor 11 is shown in FIG. 3. In the present embodiment, a thermistor in which its resistance varies with the temperature is employed as the temperature sensor. The change of temperature in the environment results the change of the resistance of the thermistor $R_T$. The change of thermistor $R_T$ can be represented by the voltage output. The control unit 20 receives the output voltage Vo1. The output of the temperature sensor belongs to a chain of periodic signals, whereas the frequencies of the periodic signals are temperature dependent. The control unit 20 detects the frequency of the waveform and determines the measured temperature.

Figure 4:
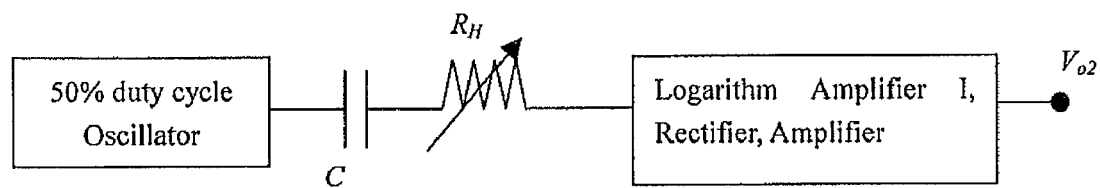
FIG. 4 depicts a circuit diagram for relative humidity sensor in the environmental device of the present invention.

FIG. 4 indicates the circuit for the relative humidity sensor 12. In the present embodiment, the relative humidity sensor 12 belongs to a resistive type relative humidity sensor. A capacitor C is connected in series to a humidity sensitive resistor $R_H$. The circuit amplifies and blocks out all DC component of the signals obtained from the sensor. The signal is output as voltage. The circuit is effective to block off the entire DC component and protect the humidity sensitive resistor $R_H$. It is a simple circuit and adaptive to different duty cycles of the input signals. In the present embodiment, a 50% oscillation duty cycle is employed.

Figure 5:
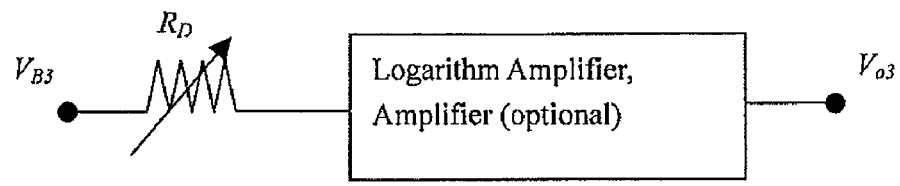
FIG. 5 depicts a circuit diagram for volatile organic compounds sensor in the environmental device of the present invention.

FIG. 5 indicates the circuit for the sensor of volatile organic compounds 13. In the present embodiment, the sensor of volatile organic compounds 13 belongs to a heated metal oxides type. The sensor varies its resistance $R_D$ with the concentration of volatile organic compounds. The input voltage $V_{B3}$ would first go through the resistor with resistance $R_D$, it will then be amplified by an analog amplifier. The voltage output is then sent to the control unit.

Figure 6:
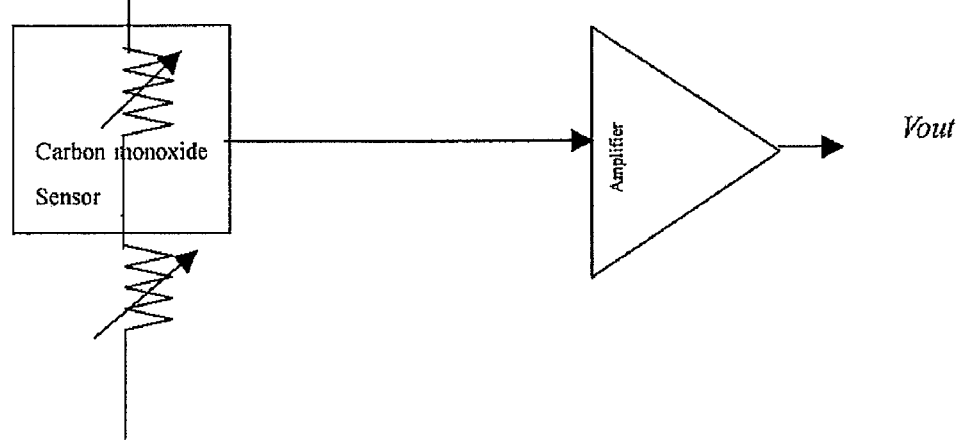
FIG. 6 depicts a circuit diagram for carbon monoxide sensor in the environmental device of the present invention.

FIG. 6 indicates the circuit for the carbon monoxide sensor 14. In the present embodiment, the carbon monoxide sensor 14 being employed belongs to a heated metal oxide type sensor. The sensor varies its resistance with the concentration of carbon monoxide. The input voltage would first go through the resistor, it will then be amplified by an analog amplifier. The voltage output is then sent to the control unit.

Figure 7:
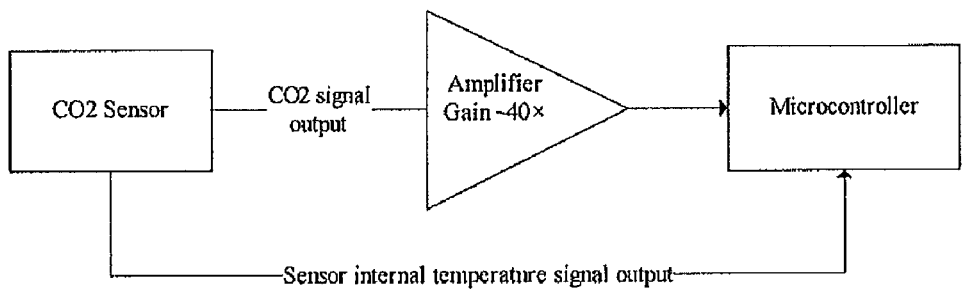
FIG. 7 depicts a circuit diagram for carbon dioxide sensor in the environmental device of the present invention.

FIG. 7 indicates the circuit of carbon dioxide sensor 15. In the present embodiment, the carbon dioxide sensor 15 belongs to a heated metal oxide type. A heating element is included in addition to the sensor element. The resistance of the sensor changes with the concentration of carbon dioxide. The input voltage first go through the resistor, it will then be amplified by an analog amplifier and be sent to the control unit 20. In order to obtain an accurate value for carbon dioxide, the desired operation temperature of the sensor is maintained by the built-in heater. The influence of the environmental temperature and ambient carbon dioxide is eliminated by comparing the voltage output obtained with that of the ambient air. A more accurate result is obtained. In addition, the internal temperature of the sensor by the heating element is fed to control unit 20. This acts as a reference for showing that the sensor has been warmed-up, and indicating that sensor has reached the optimal operation temperature.

FIG. 8 indicates the circuit for the dust sensor 16 in the present embodiment. In the present embodiment, the dust sensor 16 belongs to a light scattering type sensor. The output of dust sensor will go to low voltage (ground level) when the particulate matters are detected, otherwise the output will stay at high voltage. In other words, the low pulse occupancy time is proportional to dust concentration. By obtaining the ratio of the time of total low pulse and total high pulse, the control unit 20 would be able to calculate the corresponding dust level.

The control unit 20 in the present embodiment comprises a power supply and control circuit 21, a voltage input circuit 22, a central processing unit 23, a memory unit 24 and a voltage output circuit 25. The power supply and control circuit 21 connect an external power supply to the device. The external power supply could be either AC or DC power supply. When inserting a power plug to the present embodiment, the auto power source selector directs the power source to transformer.

The voltage input circuit 22 collects the values obtained from the sensors 10. In the present embodiment, the voltage input circuit 22 includes an analog to digital converter 26 and a low pulse time counter 27. The analog to digital converter 26 receives the analogue signals from the temperature sensor 11, the relative humidity sensor 12, the volatile organic compounds sensor 13, the carbon monoxide sensor 14, and the carbon dioxide sensor 15, as well as the reference signals by the carbon dioxide sensor 15. The analog to digital converter 26 converts the analogue signals to digital signals, and inputs the digital signal into the central processing unit 23. The low pulse time counter 27 obtains the input signal from the dust sensor circuit. The central processing unit 23 collects an average value of low pulse timing from dust sensor circuit. The types of sensors employed determine the voltage input circuit. The voltage input circuit can be modified to fit with different sensors types.

The memory unit 24 stores the first judgment principle, the second judgment principle and the third judgment principle, as well as the user-friendly interpretation of the obtained values based on the parameter ranges and recommendations in response to the obtained values based on the parameter ranges that is easily understood by a non-technical user;

The first judgment principle defines at least two-parameter ranges for each environmental parameter. The values of environmental parameter refer to the values obtained by the sensors 10, such as the values obtained by the temperature sensor, the relative humidity sensor, the volatile organic compounds sensor, the carbon monoxide sensor, the carbon dioxide sensor and the dust sensor in the present embodiment. For example, the parameter ranges for the temperature could be referred to the ranges of ">25.5° C.", "<20° C." and "<10° C." etc. The second judgment principle defines at least one the conditional arrays, the at least two parameter ranges defined by the first judgment principle for use as the parameter ranges for defining each conditional array. For example, the parameter range for the temperature in an occasion is defined as "25.5-35° C." and the parameter range for the volatile organic compounds in the same occasion is defined as ">600 µg/m³". A parameter range defined by the first judgment principle can applied for defining different conditional arrays. Air-quality-level judgment standards for air quality levels are defined based on the combination of different categories of the measured environmental parameters The messages provided include the message corresponding to the potential problems based on the parameter ranges, the recommendations to address the potential problems and the message corresponding to the air quality level. For example, as indicated in FIG. 9, when the parameter range of temperature is defined as ">25.5° C.", the recommendation in response to the obtained values based on the parameter range is "Turn on air cooling devices". A message corresponding to potential problems for each conditional array is provided, based on the second judgment principle. Referring to FIG. 10, for example, when the temperature is in the parameter range of "25.5-35° C." and the level of the total volatile organic compounds is in the parameter range of "above 600 µg/m³", the message corresponding to the potential problem for t his conditional array is "high level of formaldehyde". The recommendations to address the potential problem comprise "Open the windows", "Turn on air filtration device", "Turn on air exhausting system" and "Do not smoke". FIGS. 12 and 13 indicate the air quality level, which is defined by the air-quality-level judgment standards based on the third judgment principle.

The central processing unit 23 receives the signals from the voltage input circuit 22. The voltage input circuit 22 converts all analogue signals from the sensor circuit 20 into digital signals.

The digital signals are then judged against with the predetermined standards and criteria, which are stored in the memory unit 24 under the first judgment principle defining and obtaining the parameter range. Recommendations are provided.

The obtained values are also judged against with the predetermined standards and criteria which are stored in the memory unit 24 under the second judgment principle. The second judgment principle defines the conditional arrays. At least two parameter ranges defined by the first judgment principle for use as the parameter ranges for defining each conditional array. Based on the interrelationship of the obtained values of the different environmental parameters, a message corresponding to the potential problem for the conditional array and recommendations to address the potential problems are provided.

The obtained values are also judged against with the predetermined standards and criteria which are stored in the memory unit 24 under the third judgment principle. The air-quality-level judgment standards for air quality level are defined based on the combination of different categories of the measured environmental parameters. A message corresponding to air quality level by the air-quality-level judgment standards is provided, The display unit 30 output the individual measured values and the messages by the voltage output circuit 25, The displays are in any formats, wordings, numerical, and graphical characters.

The device of the present invention contains input ports and input/output ports, whereas the input ports receive input signal from the keypad. The input/output ports transfer the information to other devices, such as computer, pocket size personal computer and flash memory. The input/output ports connect the device to other devices by an infra-red interface device, bluetooth interface device and other wireless interface devices.

Figure 14:
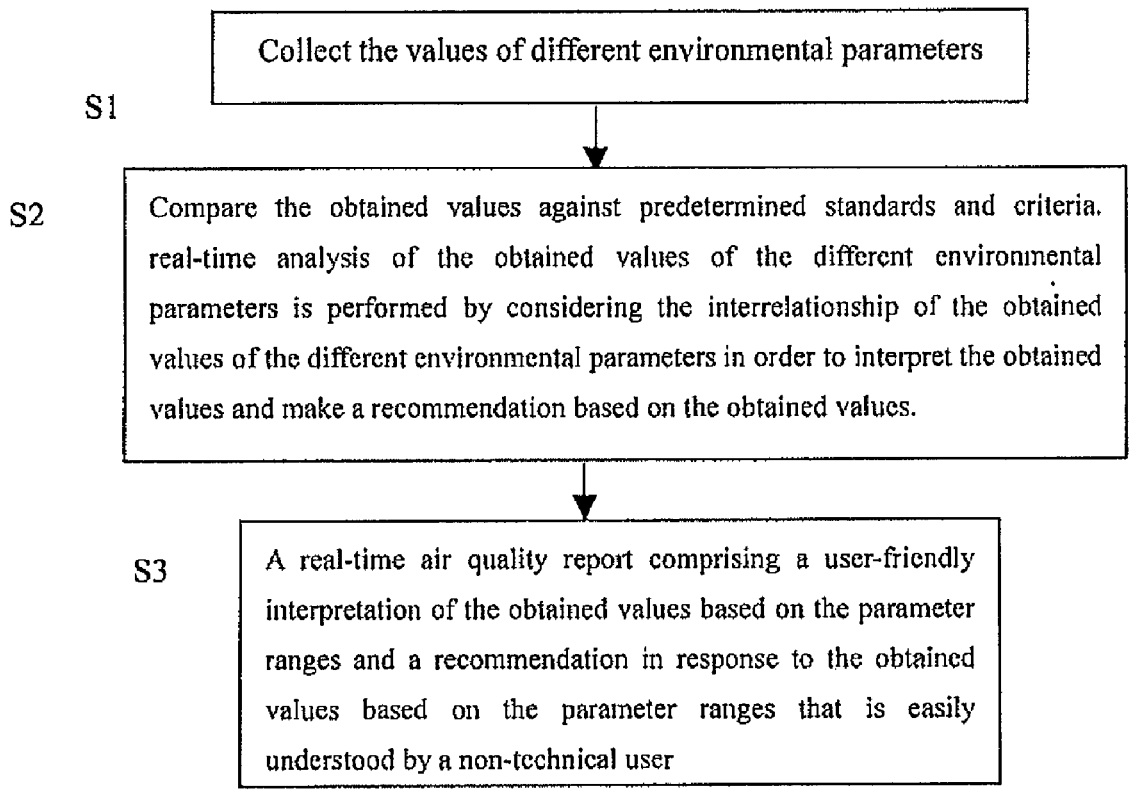
FIG. 14 depicts a flowchart of the environmental monitoring and analyzing by the present invention.

FIG. 14 indicates the method of environmental monitoring and analyzing by the present invention. The sensors S1 obtain values of different environmental parameters. The values are then sent to the control unit. The control unit in S2 compares the obtained values of the environmental parameters against the predetermined standards and criteria. Based on the interrelationship of the obtained values of the different environmental parameters, real-time analysis of the obtained values of the different environmental parameters is performed. A user-friendly interpretation of the obtained values based on the parameter ranges and recommendations in response to the obtained values based on the parameter ranges are output and displayed in the display unit S3. The first judgment principle defines the parameter ranges for each measured environmental parameter. The second judgment principle defines the conditional arrays. At 1 east two parameter ranges defined by the first judgment principle are employed the parameter ranges for defining each conditional array. The third judgment principle defines the categories for each measured environmental parameter. An overall air quality level is defined by the air-quality-level judgment standards based on the combination of different categories of the measured environmental parameters. A message corresponding to air quality level by the air-quality-level judgment standards is provided.

The invention claimed is:

1. An environmental monitoring device, comprising:
    a plurality of sensors being of different types, the different types of sensors obtaining values of different environmental parameters;
    a control unit to receive the obtained values of the environmental. parameters and to compare the obtained values against predetermined standards and criteria which define parameter ranges of the different environmental parameters; and
    a display unit to display a real-time air quality report comprising:
        a user-friendly interpretation of the obtained values based on the parameter ranges;
        a simultaneous forecast to provide an instant level assessment of at least one environmental parameter not obtained by the plurality of sensors including at least one selected from the group consisting of: formaldehyde, airborne bacteria, radon and nitrogen monoxide; and
        a recommendation in response to the obtained values based on the parameter ranges that is easily understood by a non-technical user;
    wherein real-time analysis of the obtained values of the different environmental parameters is performed by considering the interrelationship of the obtained values of the different environmental parameters in order to interpret the obtained values and make a recommendation based on the obtained values.

2. The device according to claim 1, wherein the predetermined standards and criteria includes a first judgment principle, the first judgment principle defining at least two parameter ranges for each environmental. parameter, and a corresponding recommendation for each parameter range.

3. The device according to claim 2, wherein the predetermined standards and criteria includes a second judgment principle, the second judgment principle defining at least one conditional array, the at least two parameter ranges defined by the first judgment principle are used as the parameter ranges for defining each conditional array, and a message corresponding to potential problems for each of the at least one conditional array is provided.

4. The device according to claim 3, further comprising a recommendation to address the potential problems.

5. The device according to claim 1, wherein the predetermined standards and criteria includes a third judgment principle, the third judgment principle defining at least two categories for each environmental parameter, and air-quality-level judgment standards for air quality levels are defined based on the combination of different categories of the measured environmental parameters, and a message corresponding to air quality level by the air-quality-level judgment standards is provided.

6. The device according to claim 1, wherein the environmental parameter is any one from the group consisting of: temperature, relative humidity, volatile organic compounds, carbon monoxide, carbon dioxide, dust, ozone, carbon dioxide, air flow rate, radon, and formaldehyde.

7. The device according to claim 1, wherein the control unit comprises:
    a power supply;
    control circuit;
    input circuits;

output circuit;

a central processing unit; and a memory to store the predetermined standards and criteria for judging the environmental parameters, messages corresponding to interpretations, recommendations and potential problems of the parameter ranges;

the power supply and control circuit connecting an external power supply to the device;

the input circuit collecting the obtained values from the sensors and outputting them to the central processing unit;

the central processing unit analyzing the obtained values based on the predetermined standards and criteria and defining the parameter ranges of each environmental parameter, and to output the interpretation and recommendation of each parameter range for display by the display unit.

8. The device according to claim 7, wherein the input circuit includes an analog to digital converter and a low pulse timer.

9. An environmental monitoring method, comprising:

obtaining values of environmental parameters;

comparing the obtained values of the environmental parameters against predetermined standards and criteria which define parameter ranges of the different environmental parameters in a control unit; and displaying a real-time air quality report from a display unit comprising:
- a user-friendly interpretation of the obtained values based on the parameter ranges;
- a simultaneous forecast to provide an instant level assessment of at least one environmental parameter not obtained by a sensor including at least one selected from the group consisting of: formaldehyde, airborne bacteria, radon and nitrogen monoxide; and
- a recommendation in response to the obtained values based on the parameter ranges that is easily understood by a non-technical user;

wherein real-time analysis of the obtained values of the different environmental parameters is performed by considering the interrelationship of the obtained values of the different environmental parameters in order to interpret the obtained values and make a recommendation based on the obtained values.

10. The method according to claim 9, wherein the predetermined standards and criteria include a first, second and third judgment principle, the first judgment principle defining parameter ranges for the environmental parameters, the second judgment principle defining conditional arrays, and at least two parameter ranges defined by the first judgment principle for use as parameter ranges for defining each conditional array, the third judgment principle defining at least two categories for each environmental parameter, and air-quality-level judgment standards for air quality levels are defined based on the combination of different categories of the obtained values, and a message corresponding to air quality level by the air-quality-level judgment standards is provided.

11. The method according to claim 10, wherein the environmental parameter is any one from the group consisting of: temperature, relative humidity, volatile organic compounds, carbon monoxide, carbon dioxide, dust, ozone, carbon dioxide, air flow rate, radon, and formaldehyde.

* * * * *